(12) United States Patent
Payne (10) Patent No.: US 7,370,653 B2
(45) Date of Patent: May 13, 2008

(54) CLOSURE DEVICES FOR ACCESS PORTS OF RESPIRATORY APPARATUSES

(75) Inventor: Simon Robert Payne, Surrey (GB)

(73) Assignee: Intersurgical AG, Vadux (LI)

( * ) Notice: Subject to any disclaimer, the term of this patent is extended or adjusted under 35 U.S.C. 154(b) by 0 days.

(21) Appl. No.: 10/740,165

(22) Filed: Dec. 17, 2003

(65) Prior Publication Data

US 2004/0168690 A1  Sep. 2, 2004

(30) Foreign Application Priority Data

Dec. 21, 2002  (GB) ................................ 0229870.1

(51) Int. Cl.
*A61M 16/00* (2006.01)
*A62B 9/04* (2006.01)

(52) U.S. Cl. .................... 128/207.14; 128/200.26; 128/202.27; 128/912

(58) Field of Classification Search ........... 128/200.26, 128/207.14, 207.16, 912, 202.27; 215/320, 215/358, 364; 220/234, 237, 254.1, 254.7
See application file for complete search history.

(56) References Cited

U.S. PATENT DOCUMENTS

| | | | |
|---|---|---|---|
| 3,258,178 A * | 6/1966 | Gran ........................... 222/482 |
| 3,707,972 A * | 1/1973 | Villari et al. ................. 604/249 |
| 3,741,217 A * | 6/1973 | Ciarico ........................ 604/256 |
| 3,814,103 A * | 6/1974 | Fettel et al. ............. 128/207.18 |
| 4,187,964 A * | 2/1980 | Bogart ........................ 222/546 |
| 4,240,417 A | 12/1980 | Holever |
| 4,349,024 A * | 9/1982 | Ralston, Jr. .................. 604/403 |
| 4,416,273 A * | 11/1983 | Grimes .................. 128/207.16 |
| 4,456,140 A * | 6/1984 | Geiger ........................ 215/364 |
| 4,502,606 A * | 3/1985 | Shillington et al. ......... 215/274 |
| 4,510,933 A * | 4/1985 | Wendt et al. .......... 128/207.14 |
| 4,653,477 A * | 3/1987 | Akui et al. .................. 600/154 |
| 4,674,640 A | 6/1987 | Asa et al. |
| 4,715,360 A * | 12/1987 | Akui et al. .................. 600/154 |
| 4,793,502 A | 12/1988 | Beck |
| 5,203,467 A * | 4/1993 | Tucker ..................... 220/254.3 |
| 5,354,267 A * | 10/1994 | Niermann et al. ............ 604/32 |
| 5,357,946 A | 10/1994 | Kee et al. |
| 5,382,242 A * | 1/1995 | Horton et al. ............... 604/256 |
| 5,404,873 A * | 4/1995 | Leagre et al. .......... 128/204.18 |
| 5,632,396 A * | 5/1997 | Burns .......................... 215/247 |
| 5,674,209 A * | 10/1997 | Yarger ........................ 604/540 |
| 5,735,271 A * | 4/1998 | Lorenzen et al. ....... 128/207.16 |
| 5,775,325 A * | 7/1998 | Russo .................... 128/205.12 |
| 5,890,488 A * | 4/1999 | Burden .................. 128/200.26 |
| 6,086,529 A | 7/2000 | Arndt |
| 6,409,220 B1 * | 6/2002 | Wing et al. .................... 285/12 |

(Continued)

FOREIGN PATENT DOCUMENTS

DE  40 36 361 A 1  7/1991

(Continued)

*Primary Examiner*—Danton DeMille
(74) *Attorney, Agent, or Firm*—Nixon Peabody LLP (57) ABSTRACT

A closure device (10) is disclosed for use with an access port (62,72,82,92) of a medical respiratory apparatus (60,70,80, 90). The closure device (10) comprises a cap (14) that seals the access port (62,72,82,92) save for an opening (28) in the cap (14), and a closure (16) for sealing the opening (28). The cap (14) includes a portion of flexible material (26) in which the opening (28) is formed, and is hingedly mounted with respect to the access port (62,72,82,92).

31 Claims, 6 Drawing Sheets

U.S. PATENT DOCUMENTS 6,588,421 B1 * 7/2003 Diehl et al. ............. 128/201.13
6,769,430 B1 * 8/2004 Carlsen et al. ......... 128/201.13
6,948,643 B1 * 9/2005 Lohrman .................... 222/556

FOREIGN PATENT DOCUMENTS

| | | |
|---|---|---|
| FR | 2 662 144 A1 | 11/1991 |
| GB | 2 199 630 A | 7/1988 |
| GB | 2 288 740 A | 11/1995 |
| WO | WO 90/05556 | 5/1990 |
| WO | WO 97/22535 | 6/1997 |
| WO | WO 02/36191 A2 | 5/2002 |

* cited by examiner

CLOSURE DEVICES FOR ACCESS PORTS OF RESPIRATORY APPARATUSES

This invention relates to closure devices for use with access ports of medical respiratory apparatus.

A typical medical respiratory apparatus comprises many cooperating components forming sealed conduits through which inhaled and exhaled gases flow. These components are typically of tubular construction and include junction components which fit together to form different arrangements of sealed conduits.

There are many applications of medical respiratory apparatus which require the insertion of ancillary devices into the gas within the conduits of the apparatus. Such applications include pressure monitoring, temperature monitoring, suctioning, gas sampling and fibre optic bronchoscopy. Typical medical respiratory apparatus therefore includes at least one port allowing access to the gas within the conduits. These access ports are typically sealed when not in use by closures of elastomeric material.

For suctioning, a suction catheter is inserted through an access port and into a conduit. This access port must be large enough (typically of the order of 8 mm) to allow the suction catheter to be inserted into the conduit without contacting an interior surface of the component. This is because any contact between the catheter and the component may cause a build up of secretions on the internal surface of the component. In contrast, for fibre optic bronchoscopy, a fibre optic bronchoscope of typical diameter 6 mm needs to be inserted through the access port and into the conduit whilst maintaining effective sealing of the conduit.

Conventionally, access ports are included in certain components of medical respiratory apparatus which are intended to allow the two applications specified above to be possible. This is achieved by firstly providing an access port in a component which is sufficiently large to allow suctioning as described above. A separate closure device is then provided including a cap of elastomeric material which seals the access port save for an aperture in the cap, the aperture being the correct size to allow the sealed insertion of the fibre optic bronchoscope as described above. This closure device also includes a plug for sealing the aperture when the port is not in use.

Alternatively, the aperture provided in the cap may be replaced by a duck bill valve which is normally sealed but can flex to allow the fibre optic bronchoscope to be inserted into the conduit whilst maintaining an effective seal.

Disadvantages of conventional closure devices include the awkwardness of removing and replacing the cap and/or plug. There is also a likelihood of the cap and/or plug not being replaced properly and the apparatus therefore not being properly sealed.

There has now been devised an improved closure device which overcomes or substantially mitigates the above-mentioned and/or other disadvantages of the prior art.

According to a first aspect of the invention, there is provided a closure device for use with an access port of a medical respiratory apparatus, the closure device comprising a cap for sealing the access port save for an opening in the cap, and a closure for sealing the opening, the cap including a portion of flexible material in which the opening is formed, and the cap being hingedly mounted with respect to the access port.

According to a further aspect of the invention, there is provided medical respiratory apparatus comprising an access port and a closure device as described above.

The closure device and medical respiratory apparatus according to the invention are advantageous principally because the hingedly mounted cap is guided into and out of engagement with the access port. This reduces the risk of the cap not being replaced properly or being detached from the medical respiratory apparatus and lost.

By "the cap is hingedly mounted with respect to the access port" is meant that the cap is mounted so as to be rotatable relative to the access port about a single hinge axis.

The closure device may be integrally formed with the apparatus or may be formed as a separate component that is engageable with the remainder of the apparatus. The cap may therefore be hingedly mounted on, and formed integrally with, the apparatus, or the cap may be mounted on a support body of the closure device that is engageable with the remainder of the apparatus.

The cap is preferably connected to the apparatus or support body by at least one hinge, and most preferably by at least two separate hinges which hinge about the same hinge axis. Such a construction greatly reduces lateral movement of the cap with respect to the port, thereby enabling the cap to be urged into engagement with the port by a user using only one hand.

The hinge mechanism preferably comprises one or more arms attaching the cap to the apparatus or support body. Preferably, each hinge is formed by a narrow transverse portion of reduced thickness on each arm. The cap is preferably movable between an open position, in which the access port is not obstructed, and a closed position in which the access port is sealed save for the opening in the cap. The cap is preferably rotated from its closed position to its open position through an angle of 90° or greater, more preferably 135° or greater, and most preferably approximately 180°. Such an arrangement reduces the risk of the cap obstructing the access port during use.

The cap is preferably resiliently biased towards both the open position and the closed position by means of a resilient member that forms part of the closure device. The resilient member is preferably arranged such that it is subjected to a gradually increasing tension as the cap is urged by a user away from either the open or closed position and a maximum tension when the cap is at a position approximately midway between the open and closed positions. The resilient member is preferably a band of resilient material and is preferably disposed between the cap and the apparatus or support body. Typically, the resilient member is integrally formed with the cap and is sufficiently thin so as to be flexible.

In use, when the resilient member is urged by a user away from the open position and towards the closed position, the resilient member applies a rotational force on the cap which urges the cap back towards the open position. However, if the tensioned resilient member passes through the hinge axis of the cap, the tensioned resilient member will apply an opposite rotational force on the cap which will urge the cap towards the closed position instead. If the cap is released at this point by the user, the cap will close with a positive action. The resilient member has the same action when the cap is urged from the closed position to the open position. Such a hinge mechanism therefore provides the cap with a positive opening and closing action which speeds up the opening and closing of the cap, and reduces the risk of the cap being inadvertently displaced from either the open or closed position.

The closure device preferably comprises a support body which is adapted to be closely received, in use, internally or externally of the access port. Preferably, the support body is adapted to be closely received, in use, internally of the access port and preferably includes elastomeric sealing rings which ensure an effective seal between the support body and the access port. Preferably the support body and the access port are cylindrical.

The cap preferably comprises a portion of relatively rigid plastics material and the portion of flexible material which is most preferably elastomeric material. These materials may be any such materials which are suitable for use in medical respiratory apparatus and together provide an effective seal. For example, the relatively rigid plastics material may be polypropylene and the elastomeric material may be a thermoplastic elastomer (TPE). The closure device is preferably formed using a two-shot injection moulding process which involves injection moulding the relatively rigid plastics material and subsequently injection moulding the elastomeric material onto the relatively rigid plastics material. This two-shot injection moulding process bonds the elastomeric material to the surface of the relatively rigid plastics material.

The portion of elastomeric material preferably includes the opening such that, in use, an effective seal is formed between the cap and any ancillary device inserted into the opening that is of greater dimensions than the opening. The relatively rigid plastics portion is preferably integrally formed with the apparatus or support body. The elastomeric material is preferably sufficiently flexible to allow a variety of ancillary devices of varying diameters greater than that of the opening to be inserted with a tight fit into the opening.

The closure is preferably hingedly mounted with respect to the opening, and most preferably hingedly attached to the cap. The closure preferably comprises a plug which is dimensioned to be received within the opening with a tight fit and thereby form an effective seal. The plug preferably includes an enlarged end portion which, when in engagement, projects through the opening and has a diameter greater than that of the opening such that the risk of the plug becoming loose is reduced.

The closure is preferably arranged such that the closure is movable between an open position, in which the opening is not obstructed, and a closed position, in which the opening is sealed by the plug. The closure is preferably hingedly attached to the cap at the opposite side of the cap to that at which the cap is hingedly mounted to the apparatus or support body. This feature allows the closure to be disengaged from the cap without the cap consequently being urged away from the apparatus or support body.

The invention will now be described in greater detail, by way of example only, with reference to the accompanying drawings, in which.

Figure 1:
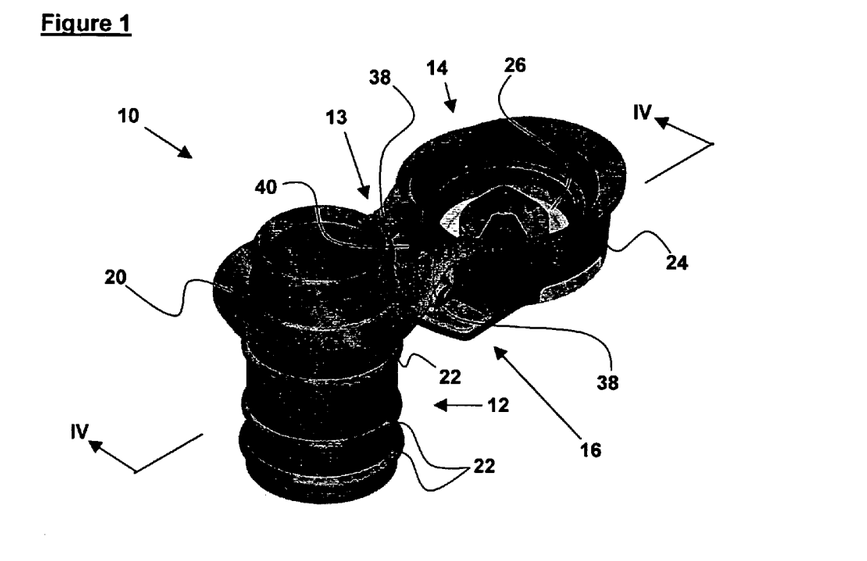
FIG. 1 is a perspective view of a closure device according to the present invention in a fully open position.
Figure 2:
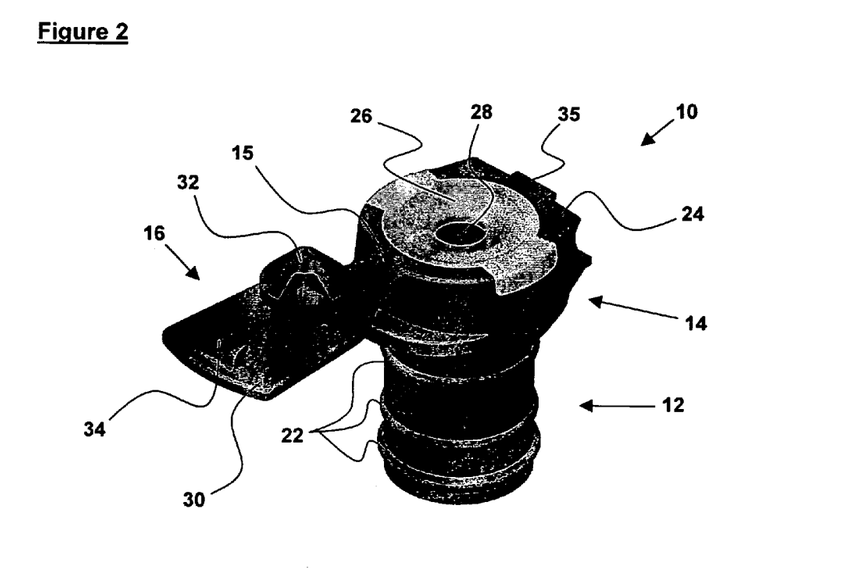
FIG. 2 is view similar to that of FIG. 2 with the closure device in a partially open position.

Referring firstly to FIGS. 1 and 2, a closure device according to the present invention is generally designated 10. The closure device 10 comprises a support body 12, a cap 14 and a plug 16. The support body 12, cap 14 and plug 16 are formed integrally, the cap 14 being connected to the support body 12 by a first hinge 13 and the plug 16 being connected to the cap 14 by a second hinge 15. The closure device 10 is formed in both relatively rigid plastics material and elastomeric material, preferably by a two-shot injection moulding process. The relatively rigid plastics material is polypropylene and the elastomeric material is a thermoplastic elastomer (TPE). The two-shot injection moulding process involves injection moulding the relatively rigid plastics material and subsequently injection moulding the elastomeric material onto the relatively rigid plastics material so that the two materials are integrally bonded.

The support body 12 comprises a cylinder which is open at both ends and is formed in a relatively rigid plastics material. The support body 12 has an upper end portion which tapers inwards slightly towards its upper end (see FIG. 4). This upper end portion includes an outwardly extending sealing rib 18 at its rim. Below the rim, the support body 12 has a radially extending flange 20. Below this flange 20, the external surface of the cylinder has a number of integrally moulded sealing rings 22 of elastomeric material.

The cap 14 has an upper surface comprising an outer portion 24 of relatively rigid plastics material and an inner portion 26 of elastomeric material. The inner portion 26 comprises a disc of elastomeric material with a central circular aperture 28 and two wings, which are moulded into corresponding recesses in the outer portion 24. The elastomeric material of the inner portion 26 is sufficiently flexible to allow a variety of ancillary devices of varying diameters to be inserted with a tight fit into the aperture 28.

The plug 16 comprises a flap 30 which is generally rectangular and planar in shape and is connected to the cap 14 by the second hinge 15. The second hinge 15 comprises a transverse region of the flap 30, located at its junction with the cap 14, which is of greatly reduced thickness such that the plug 16 can hinge about this region. There is a plug body 32 on the upper surface of the plug 16 (as viewed in FIG. 2). The plug body 32 comprises a cylindrical stem, an enlarged cylindrical portion above the stem and a conical formation in the shape of a cross above the enlarged cylindrical portion.

The plug 16 is arranged such that, when the plug 16 is rotated about the second hinge 15, the conical formation and the enlarged cylindrical portion of the plug body 32 may be forced through the aperture 28, thereby engaging the plug 16 with the cap 14. The plug 16 further includes a hook 34 which, when the plug 16 is engaged with the cap 14, engages a corresponding ridge 35 formed on the cap 14. In addition, the plug 16 is dimensioned such that, when the plug 16 and cap 14 are engaged, the plug 16 extends beyond the periphery of the cap 14, thereby facilitating disengagement of the plug 16 from the cap 14. The second hinge 15 is located at the opposite side of the cap 14 to the first hinge 13. This feature allows the plug 16 to be disengaged from the cap 14 without the cap 14 consequently being urged away from the support body 12.

FIG. 1 shows the closure device 10 in a fully open position. In this position, the cap 14 is disengaged with the support body 12 and positioned such that the open upper end of the support body 12 is not obstructed. The closure device 10 in the fully open position is therefore suitable for receiving a suction catheter when the closure device 10 forms part of a medical respiratory apparatus. The plug body 32 of the plug 16 may be engaged with the aperture 28 of the cap 14, as shown in FIG. 1.

FIG. 2 shows the closure device 10 in a partially open position which is suitable for receiving a fibre optic bronchoscope when the closure device 10 forms part of a medical respiratory apparatus. In this position, the cap 14 is engaged with the upper end of the support body 12 but the plug body 32 of the plug 16 is disengaged from the cap 14. The sealing rib 18 of the support body 12 is received with a snap fit within a corresponding recess in the internal surface of the cap 14 such that there is an effective seal between the upper end of the support body 12 and the internal surface of the cap 14.

Figure 3:
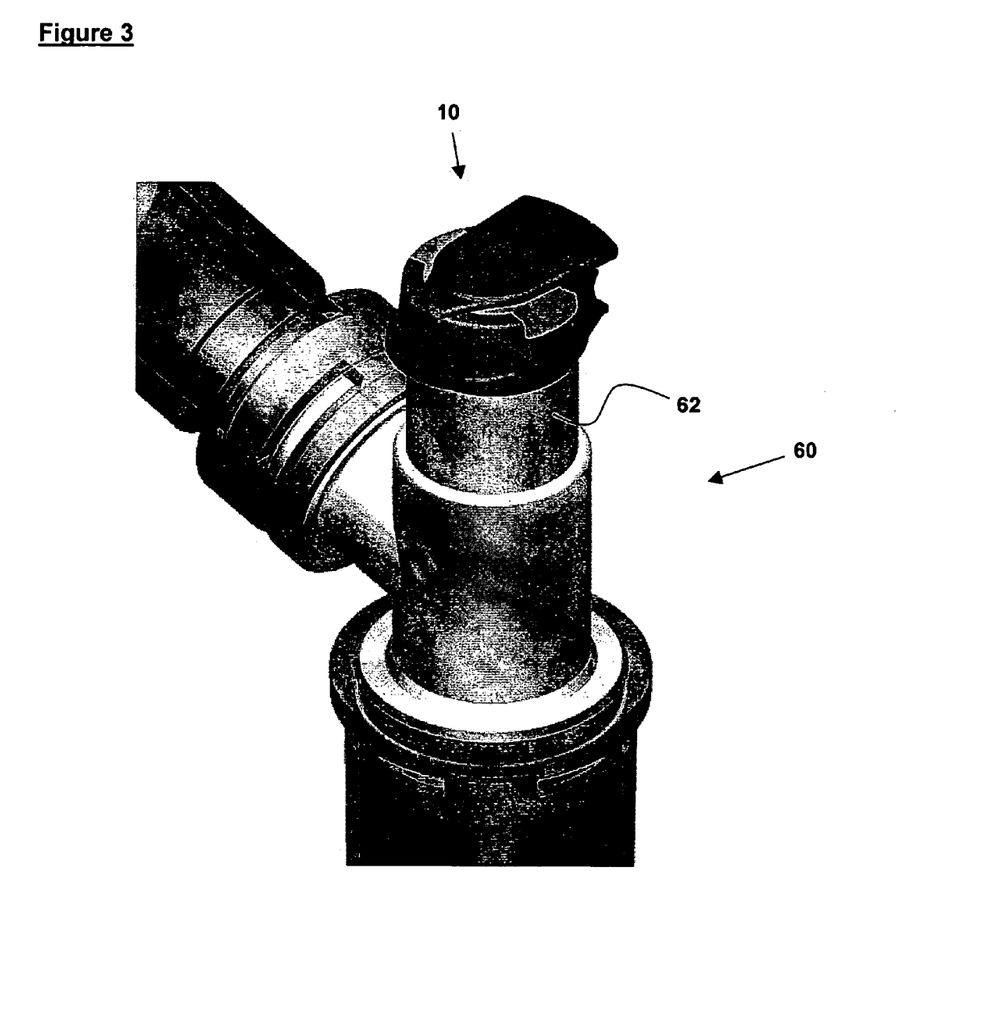
FIG. 3 is a perspective view of the closure device forming part of a first embodiment of a component of a medical respiratory apparatus, the closure device being in a closed position.

Turning now to FIG. 3, there is shown a first embodiment of a component 60 of a medical respiratory apparatus including a closure device 10 as described above. The support body 12 of the closure device 10 is closely received within a tubular port 62 of the component 60. The sealing rings 22 ensure that the interface between the external surface of the support body 12 and the internal surface of the port 62 is effectively sealed. The closure device 10 is shown in a closed position with the cap 14 engaged with the support body 12 and the plug body 32 engaged with the cap 14. In this position, the plug body 32 of the plug 16 is engaged with the cap 14 such that the stem of the plug body 32 is closely received within the aperture 28 and the enlarged cylindrical portion, together with the conical formation, of the plug body 32 is located on the opposite side of the inner portion 26 to the remainder of the plug 16. In this position, the enlarged cylindrical portion of the plug body 32 has a greater diameter than the aperture 28 such that the risk of the plug body 32 becoming loose is reduced.

Figure 4:
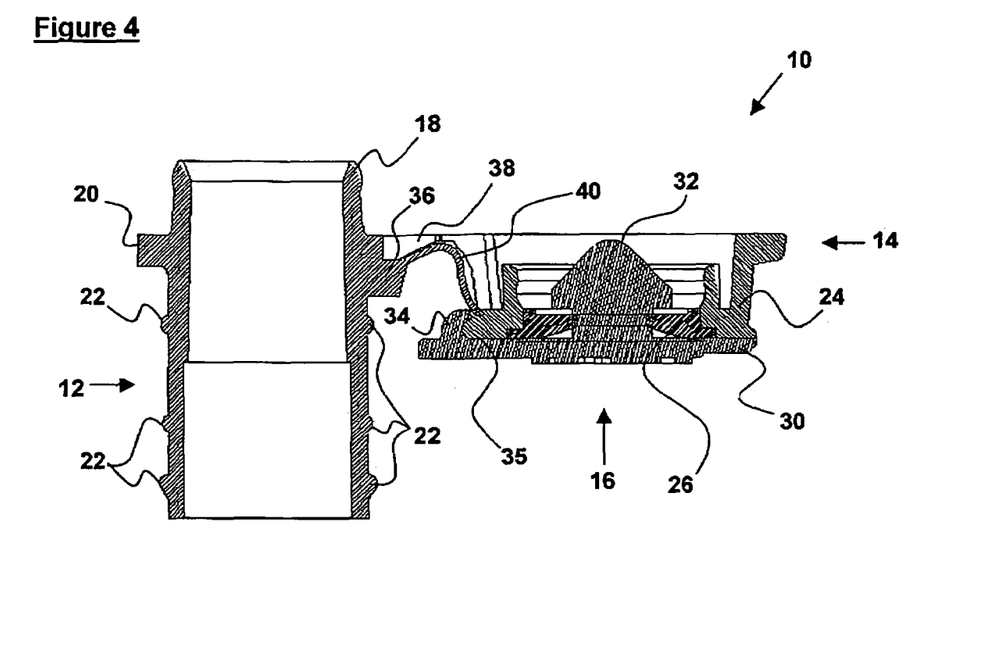
FIG. 4 is a sectional view along the line IV-IV in FIG. 1 of the closure device in the fully open position.
Figure 5:
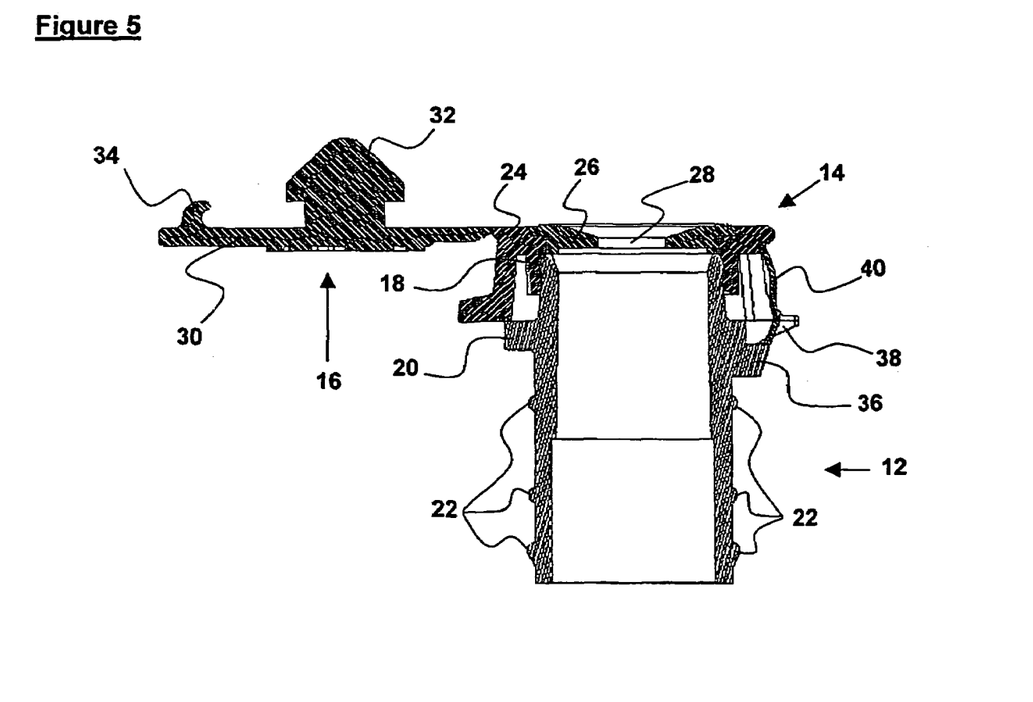
FIG. 5 is a view similar to that of FIG. 4 of the closure device in the partially open position.
Figure 6:
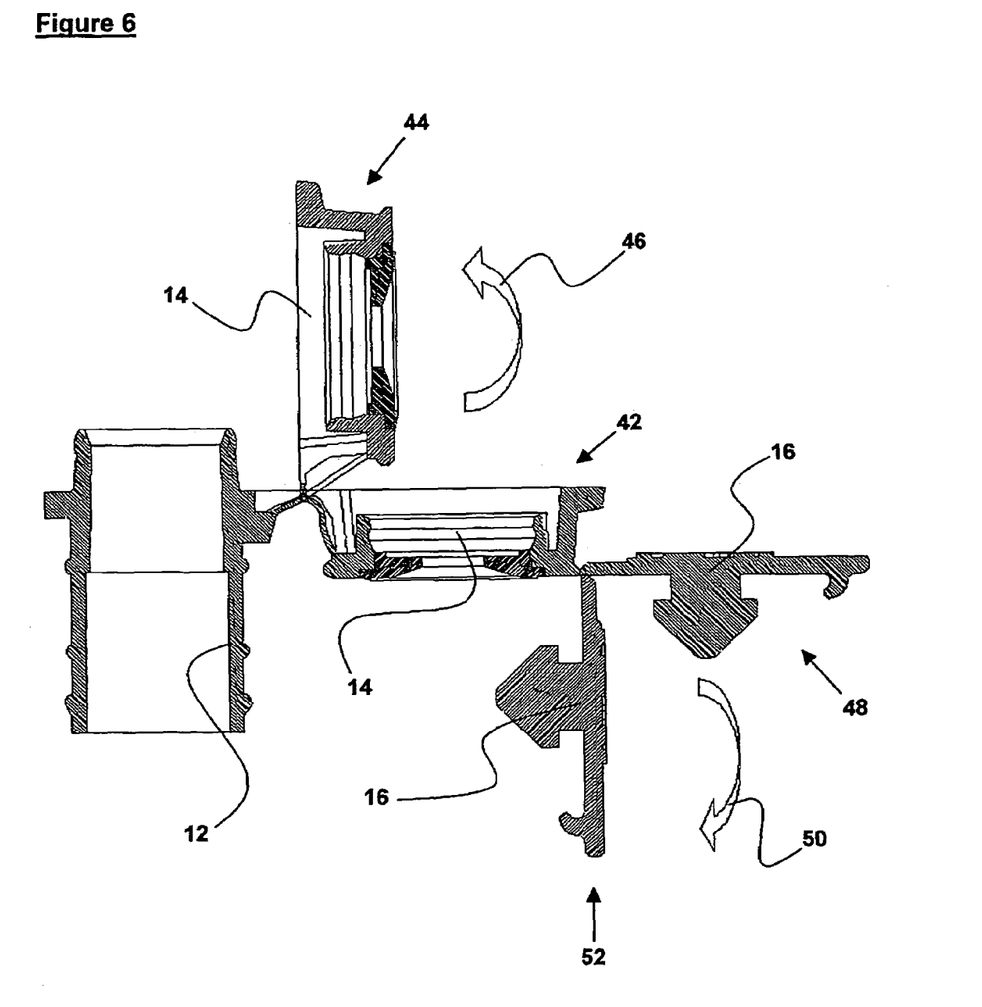
FIG. 6 is a view similar to that of FIG. 4 showing typical movement and positions enabled by first and second hinges.

Turning now to FIGS. 4, 5 and 6, the support body 12 includes a formation 36, immediately below the flange 20, which extends outwardly beyond the edge of the flange 20. The formation 36 is of a generally cubic shape. The first hinge 13 is formed by two arms 38 (also shown in FIG. 1), which extend from the flange 20, from a position either side of the formation 36, to the upper end (as viewed in FIGS. 1 and 4) of the skirt of the cap 14. The first hinge 13 further includes a relatively thin band 40 of plastics material extending from the upper end of the formation 36 of the support body 12 to the cap 14. The two arms 38 each have corresponding transverse regions of greatly reduced thickness which allow the cap 14 to hinge about these regions. The two arms 38 have the same hinge axis and because they are spaced apart, as shown in FIG. 1, lateral movement of the cap 14 with respect to the support body 12 is prevented. This feature therefore enables the cap 14 to be urged into engagement with the support body 12 by a user using only one hand.

FIG. 6 shows the cap 14 in both an open position 42 and a vertical, intermediate position 44, and the plug 16 in an open position 48 and an intermediate position 52 (for clarity, the plug 16 is omitted from the part of the drawing that shows the cap 14 in the vertical position). The band 40 is integrally formed with the remainder of the closure device 10, with a length such that, when the closure device 10 is in the fully open position 42, the band 40 is relaxed and, when the cap 14 is in the vertical position 44, the band 40 is under tension. Thus, as the cap is rotated by a user in the direction of arrow 46 from the fully open position 42, the band 40 increases in tension until the cap 14 is in the vertical position 44. When the band 40 passes the hinge axis of the cap 14, the band 40 will urge the cap 14 towards the support body 12 and will therefore contract relatively quickly if allowed to do so by the user. The band 40 therefore provides the cap 14 with a positive shutting action. The cap 14 has a similar action in the opposite direction.

The lid 14 may rotate about the second hinge 15, from open position 48, in the direction of arrow 50, through intermediate position 52, until the plug 16 engages with the cap 14. The same range of rotation is also possible in the opposite direction.

Figure 7:
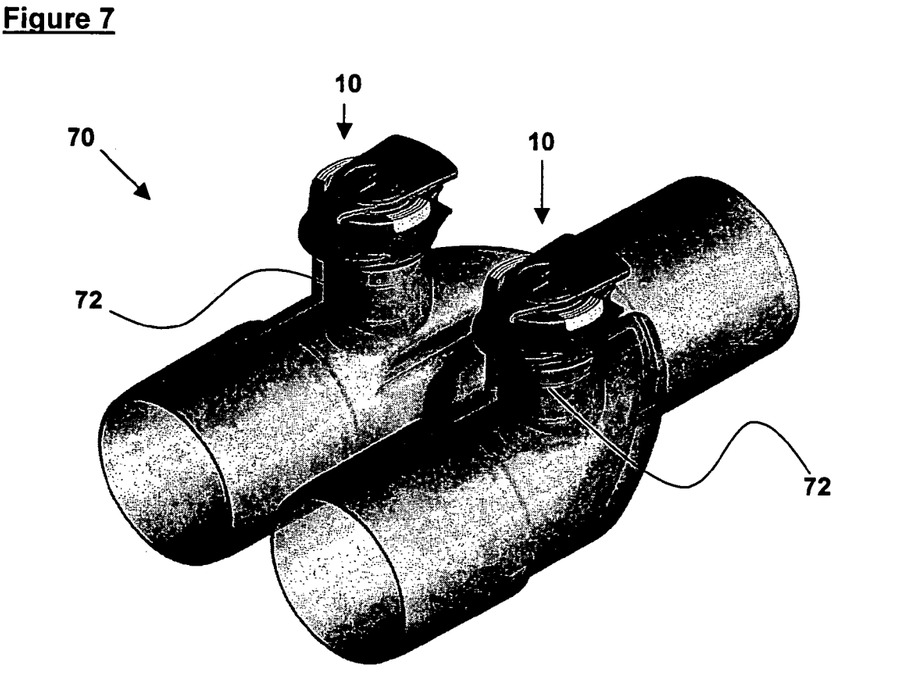
FIG. 7 is a perspective view of a second embodiment of a component of a medical respiratory apparatus according to the present invention.

Turning now to FIG. 7, a second embodiment of a component of a medical respiratory apparatus according to the present invention is commonly referred to as a Y-piece and is generally designated 70. The component 70 comprises a tubular main body, which is arranged in a Y-shape with two arms, and a tubular port 72 extending perpendicularly from each of the arms. A closure device 10 is closely received within each of the ports 72, as described above for the first embodiment.

Figure 8:
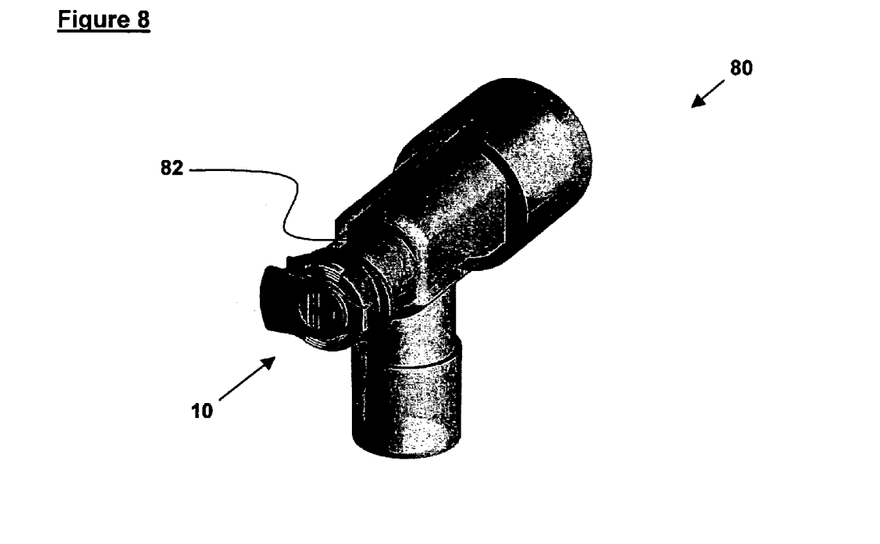
FIG. 8 is a perspective view of a third embodiment of a component of a medical respiratory apparatus according to the present invention.

Turning now to FIG. 8, a third embodiment of a component of a medical respiratory apparatus according to the present invention is a catheter mount and is generally designated 80. The component 80 comprises a tubular main body, which has two tubes arranged at an angle to each other, and a tubular port 82 extending from the end of one of the tubes. A closure device 10 is closely received within the port 82, as described above for the first embodiment.

Figure 9:
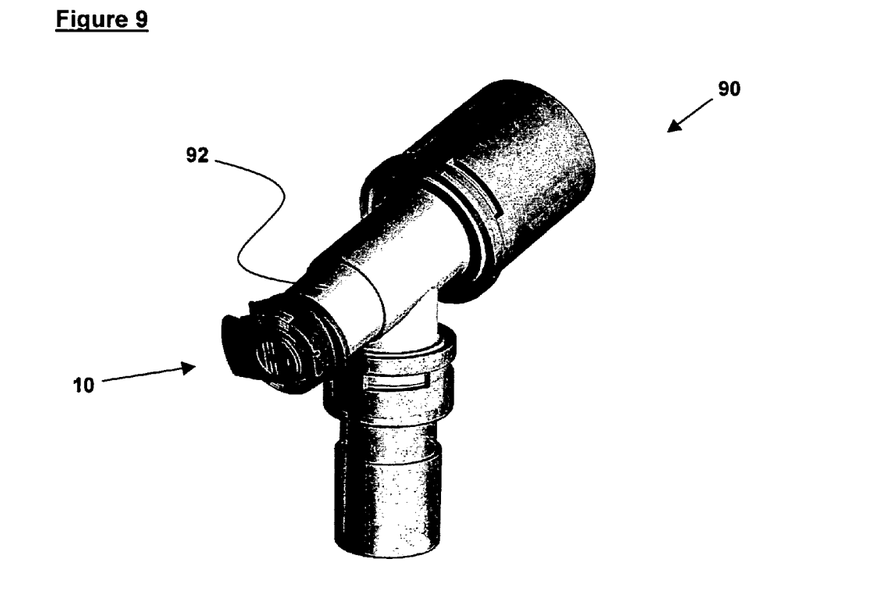
FIG. 9 is a perspective view of a fourth embodiment of a component of a medical respiratory apparatus according to the present invention.

Finally, FIG. 9 shows a fourth embodiment of a component of a medical respiratory apparatus according to the present invention that is commonly known as a swivel elbow and is generally designated 90. The component 90 is similar to the third embodiment, with a port 92 and a closure device 10, save that one of the tubes of the main body has a swivel joint.

The invention claimed is:

1. A closure device for use with an access port of a medical respiratory apparatus, the closure device comprising a cap for sealing the access port save for an opening in the cap, and a closure for sealing the opening, the cap including a portion of a first, elastomeric material in which the opening is formed, and a portion of a second, more rigid plastics material that is different from the first material, and the cap being hingedly mounted with respect to the access port so as to be rotatable relative to the access port about a single hinge axis between an open position, in which the access port is not obstructed by the cap, and a closed position in which the access port is sealed save for the opening in the cap.

2. A closure device as claimed in claim 1, wherein the cap is hingedly mounted on a support body of the closure device engageable with the medical respiratory apparatus.

3. A closure device as claimed in claim 2, wherein the support body is adapted to be closely received, in use, internally of the access port.

4. A closure device as claimed in claim 2, wherein the cap is mounted on the support body by at least one hinge.

5. A closure device as claimed in claim 4, wherein the cap is mounted on the support body by at least two separate hinges which hinge about the same hinge axis.

6. A closure device as claimed in claim 4, wherein the cap is attached to the support body by one or more arms, and each hinge is formed by a narrow transverse portion of reduced thickness on each arm.

7. A closure device as claimed in claim 1, wherein the cap is rotated from its closed position to its open position through an angle of 135° or greater.

8. A closure device as claimed in claim 1, wherein the closure device is formed using a two-shot injection moulding process which involves injection moulding the relatively rigid plastics material and subsequently injection moulding the elastomeric material onto the relatively rigid plastics material.

9. A closure device as claimed in claim 1, wherein the closure is hingedly mounted with respect to the opening.

10. A closure device as claimed in claim 9, wherein the closure is hingedly attached to the cap at the opposite side of the cap to that at which the cap is hingedly mounted to the support body.

11. A medical respiratory apparatus comprising an access port and a closure device as claimed in claim 1.

12. A medical respiratory apparatus as claimed in claim 11, wherein the closure device is integrally formed with the apparatus.

13. A medical respiratory apparatus as claimed in claim 11, wherein the closure device is formed as a separate component that is engageable with the remainder of the apparatus.

14. A closure device, for use with an access port of a medical respiratory apparatus, the closure device comprising:
a cap for sealing the access port save for an opening in the cap, and
a closure for sealing the opening,
wherein the cap includes a portion of a first, elastomeric material in which the opening is formed, and a portion of a second, more rigid plastics material that is different from the first material, and the cap being hingedly mounted with respect to the access port so as to be rotatable relative to the access port about a single hinge axis, and
wherein the cap is movable between an open position, in which the access port is not obstructed, and a closed position in which the access port is sealed save for the opening in the cap, and the cap is resiliently biased towards both the open position and the closed position by means of a resilient member that forms part of the closure device.

15. A closure device as claimed in claim 14, wherein the resilient member is arranged such that it is subjected to a gradually increasing tension as the cap is urged by a user away from either the open or closed position and a maximum tension when the cap is at a position approximately midway between the open and closed positions.

16. A closure device as claimed in claim 15, wherein the resilient member is a band of resilient material disposed between the cap and the support body.

17. A medical respiratory apparatus comprising an access port and a closure device as claimed in claim 14.

18. A closure device for use with an access port of a medical respiratory apparatus, the closure device comprising a cap for sealing the access port save for an opening in the cap, and a closure for sealing the opening, the cap including a portion of a first, elastomeric material in which the opening is formed, and a portion of a second, more rigid plastics material that is different from the first material, the first material being a thermoplastic elastomer, and the cap being hingedly mounted with respect to the access port so as to be rotatable relative to the access port about a single hinge axis between an open position, in which the access port is not obstructed by the cap, and a closed position in which the access port is sealed save for the opening in the cap.

19. A closure device as claimed in claim 18, wherein the cap is hingedly mounted on a support body of the closure device engageable with the medical respiratory apparatus.

20. A closure device as claimed in claim 19, wherein the support body is adapted to be closely received, in use, internally of the access port.

21. A closure device as claimed in claim 19, wherein the cap is mounted on the support body by at least one hinge.

22. A closure device as claimed in claim 21, wherein the cap is mounted on the support body by at least two separate hinges which hinge about the same hinge axis.

23. A closure device as claimed in claim 21, wherein the cap is attached to the support body by one or more arms, and each hinge is formed by a narrow transverse portion of reduced thickness on each arm.

24. A closure device as claimed in claim 18, wherein the cap is rotated from its closed position to its open position through an angle of 135° or greater.

25. A closure device as claimed in claim 18, wherein the cap is resiliently biased towards both the open position and the closed position by means of a resilient member that forms part of the closure device.

26. A closure device as claimed in claim 25, wherein the resilient member is arranged such that it is subjected to a gradually increasing tension as the cap is urged by a user away from either the open or closed position and a maximum tension when the cap is at a position approximately midway between the open and closed positions.

27. A closure device as claimed in claim 26, wherein the resilient member is a band of resilient material disposed between the cap and the support body.

28. A closure device as claimed in claim 18, wherein the closure device is formed using a two-shot injection molding process which involves injection molding the relatively rigid plastics material and subsequently injection molding the elastomeric material onto the relatively rigid plastics material.

29. A closure device as claimed in claim 18, wherein the closure is hingedly mounted with respect to the opening.

30. A closure device as claimed in claim 29, wherein the closure is hingedly attached to the cap at the opposite side of the cap to that at which the cap is hingedly mounted to the support body.

31. A medical respiratory apparatus comprising an access port and a closure device as claimed in claim 18.

* * * * *